(12) United States Patent
Sachse et al.

(10) Patent No.: US 6,475,515 B2
(45) Date of Patent: *Nov. 5, 2002

(54) PROCESS FOR INCREASING THE STABILITY OF LIPOSOME SUSPENSIONS THAT CONTAIN HYDROPHILIC ACTIVE INGREDIENTS

(75) Inventors: Andreas Sachse, Berlin (DE); Georg Rossling, Berlin (DE); Jens Leike, Berlin (DE)

(73) Assignee: Schering Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/652,573

(22) PCT Filed: Nov. 30, 1994

(86) PCT No.: PCT/EP94/03964

§ 371 (c)(1),
(2), (4) Date: Sep. 30, 1996

(87) PCT Pub. No.: WO95/15153

PCT Pub. Date: Jun. 8, 1995

(65) Prior Publication Data

US 2002/0102293 A1 Aug. 1, 2002

(30) Foreign Application Priority Data

Dec. 2, 1993 (DE) .......................... 43 41 472

(51) Int. Cl.[7] .............................................. A61K 9/127
(52) U.S. Cl. .................. 424/450; 424/1.21; 424/9.321; 424/9.51
(58) Field of Search .............................. 424/450, 1.21, 424/9.321, 9.51; 264/4.1, 4.3, 4.6

(56) References Cited

U.S. PATENT DOCUMENTS

| | | | | | |
|---|---|---|---|---|---|
| 4,247,411 A | * | 1/1981 | Vanlerberghe | ............... | 252/316 |
| 4,857,319 A | * | 8/1989 | Crowe | ........................ | 424/94.1 |
| 4,897,355 A | * | 1/1990 | Eppstein | .................. | 435/240.2 |
| 5,110,475 A | * | 5/1992 | Rossling | ..................... | 210/640 |
| 5,612,057 A | * | 3/1997 | Lanza | ........................ | 424/450 |

OTHER PUBLICATIONS

Margalit. J. Controlled Release 17, #3, 1991.*

* cited by examiner

*Primary Examiner*—Gollamudi S Kishore
(74) *Attorney, Agent, or Firm*—Millen, White, Zelano & Branigan, P.C.

(57) ABSTRACT

A process for increasing the stability of liposome suspensions that contain hydrophilic active ingredients is described, which is characterized in that the active ingredient that is to be encapsulated in the liposomes is metered such that 5% to 95% by weight of the active ingredient is present in unencapsulated form.

10 Claims, No Drawings

PROCESS FOR INCREASING THE STABILITY OF LIPOSOME SUSPENSIONS THAT CONTAIN HYDROPHILIC ACTIVE INGREDIENTS

This application is a 371 of PCT/EP94/03964 filed Nov. 30, 1994.

The invention relates to a process for increasing the stability of liposome suspensions that contain hydrophilic active ingredients, which is characterized in that the active ingredient that is to be encapsulated in the liposomes is metered such that 5 to 95% by weight (preferably 30 to 70% by weight) of the active ingredient is present in unencapsulated form.

The process according to the invention especially relates to those methods in which this unencapsulated active ingredient is not separated.

Hydrophilic active ingredients are to be defined as those substances according to the invention—especially pharmaceutical agents and pharmaceutical agent mixtures—that dissolve at room temperature by at least 1% by weight and preferably by at least 10% by weight in water.

Stability is to be defined according to the invention in that the product that is produced according to the process of the invention can be stored for at least 3 months, but preferably more than 6 months, at 4–8° C., without pharmaceutically unacceptable quality changes occurring.

Of course, the invention also relates to the liposome suspensions that are produced according to the process of the invention.

In recent years, liposomes have become increasingly important as potential pharmaceutical vehicles. In this connection, the possibility of using them primarily for selective transport of a pharmaceutical substance to the site of action (so-called drug targeting) is emphasized (Rubas, W., Schreier, H., Liposomen: Fortschritte in Herstellungs-Technologie und Therapie, Pharmazie Unserer Zeit [Liposomes: Improvements in Production-Technology and Therapy, Pharmaceutics of Our Time] 20, 255–270 (1991)). In targeting, a distinction is made between so-called "passive targeting" because of the liposomes being taken up in cells of the reticulo-endothelial system (RES; e.g., liver and spleen) and "active targeting," in which surface-modified liposomes are directed to the target tissue via the introduction of "homing devices" (e.g., antibodies).

In addition to this purpose, the liposomes can be used as reservoirs for the sustained release of pharmaceutical substances, or the liposomes can protect the pharmaceutical substances from quick hydrolytic or enzymatic degradation in the organism.

Liposomes are suitable for encapsulating both hydrophilic and lipophilic pharmaceutical substances. While quantitative inclusions can be obtained with lipophilic pharmaceutical substances, complete inclusion of hydrophilic pharmaceutical substances is not achieved with conventional processes. In the case of some mechanical dispersion processes, when using high lipid concentrations (up to 400 mg/ml) for certain hydrophilic substances, inclusion levels of up to 70% can be achieved. This value lies near the theoretical maximum, which can be calculated at about 74% assuming extremely close sphere packing of spheres of like size. In most cases, however, only inclusion capacities in the range of between 10 and 55% for the various liposome production processes are cited for hydrophilic pharmaceutical substances. In this case, only the so-called remote or active loading technique represents an exception (Mayer, L. D.; Bally, M. B.; Hope, M. J.; Cullis, P. R., Biochim. Biophys. Acta 816, 294–302 (1985)), in which ionizable, hydrophilic pharmaceutical agents are quantitatively conveyed to the interior of the liposome via pH gradients.

With respect to the use of such liposome preparations as pharmaceutical agents, it appears desirable for various reasons to avoid leaving a portion of pharmaceutical substance unencapsulated. Primarily in the case of encapsulation of toxic pharmaceutical substances (e.g., cytostatic agents), which often have fewer side effects in liposomal form, the overall load on the organism should be minimized by removing the unencapsulated pharmaceutical substance.

Up until now, therefore, in the standard processes for liposome production, measures have been taken to remove the unencapsulated, hydrophilic pharmaceutical substances. For this purpose, standard physical separating processes, such as, for example, centrifuging, exclusion chromatography (GPC), or membrane processes, such as dialysis or ultrafiltration, are generally used. A common feature of all these processes is that they are technically expensive and, moreover, can drastically alter the properties of the liposomes (New, R. R. C., Preparations of Liposomes, in: New, R. R. C. (Editors), Liposomes: A Practical Approach, Oxford University Press, New York, 1990, p. 91 ff).

In this way, liposome suspensions can be produced in which an approximately 100% inclusion is present immediately after separation. Due to instabilities, e.g., because of osmotic effects, however, a considerable reduction in the enclosed portion is noted even within a short time. In the case of methotrexate (MTX)-containing liposomes, in which the separation of the unencapsulated portion was carried out by centrifuging twice, the MTX-release (6° C., away from light) was, for example, about 0.2%/day (Stricker, H.; Mentrup, E.; Krotz, R.; Zeller, W. J.; Sturm, V.; Wowra, B, Eur. J. Pharm. Biopharm. 37, 175–177 (1991)). Even more drastic inclusion losses were described for liposomal dideoxyinosine triphosphate, where the inclusion losses depending on the lipid composition of the liposomes was up to 60% within one month (4° C.) (Betageri, G. V., Drug. Devel. Ind. Pharm. 19, 531–539 (1993)).

Owing to this fact, various groups were tested to determine whether, by freeze-drying, corresponding liposome suspensions can be converted to a form that is stable in storage. For this purpose, an attempt was made by suitable measures to achieve complete retention of the inclusion during freeze-drying and subsequent resuspension. In these studies, it was noted that the liposome structure can be obtained only in the presence of cryoprotectors (e.g., saccharose, trehalose) (Crow, J. H.; Crowe., L. M., et al., Biochim. Biophys. Acta 947, 367–384 (1988)).

In the presence of those additives, however, to date it has not been possible to stabilize liposome suspensions with hydrophilic pharmaceutical substances, so that the inclusion that existed before freeze-drying (>90%) was maintained. The inclusions that are obtained after resuspension are considerably below 60% (Talsma, H., Crommelin, D. J. A., Liposomes as Drug Delivery Systems, Part III: Stabilization, Pharmaceutical Technology International 5, 36–42 (1993)).

In connection with the freeze-drying of liposomes, an alternative process for the production of liposomes with hydrophilic pharmaceutical substances was recently described. In the case of these methods, referred to as "dehydration-rehydration-methods," (Kirby, C.; Gregoriadis, G., Biotechnology 2, 979–984 (1984)), an aqueous, pharmaceutical substance-containing phase is mixed with a liposome dispersion, and the mixture is freeze-dried. After rehydration of corresponding lyophilizates with small amounts of resuspension agents, MLV dispersions with inclusion capacities of up to 72% are obtained. In this connection, however, the inclusion capacities that can be achieved depend to an extreme extent on the type of pharmaceutical substance to be encapsulated. Thus, for liposomes that are produced by these methods, with nonionic x-ray contrast media, an inclusion capacity of less than 7% was described (Seltzer, St. E., Gregoriadis, G.; Dick, R., Invest. Radiol. 23, 131–138 (1988)).

With respect to providing liposomal preparations with hydrophilic pharmaceutical substances, there are still limitations with regard to determining the limited storage stability of such preparations. Thus, the corresponding liposome preparations, from which the unencapsulated pharmaceutical substance was separated before storage, had problems with respect to determining the retention of pharmaceutical substances ("leakage"). Because of leakage, the encapsulated portion of pharmaceutical substance generally decreased very quickly. It previously also was not possible to prevent this problem by the specific selection of lipid composition of the liposomes. Also, attempts to stabilize the liposome inclusion of hydrophilic substances by freeze-drying did not lead to the desired success.

With the liposome formulations according to the invention, preparations are now available for the first time which, in the case of encapsulation of hydrophilic pharmaceutical substances, exhibit adequate storage stability. Moreover, the corresponding formulations, surprisingly enough, offer additional pharmaceutical as well as therapeutical/diagnostic advantages.

In addition to the encapsulated, hydrophilic (water-soluble) pharmaceutical substance, the liposome formulations according to the invention contain an unencapsulated portion of the same. The latter can lie between 5 and 95%, but preferably between 30 and 70% of the entire amount of pharmaceutical substance present. In the formulations according to the invention, a combination of several hydrophilic pharmaceutical substances may also be present.

The water-soluble pharmaceutical substances that are contained in the preparations according to the invention may comprise, for example, vitamins, hormones, antimycotic agents, anti-allergic agents, antiphlogistic agents, antihypertensive agents, antiarrhythmic agents, antibiotics, antiviral agents, anxiolytic agents, cytostatic agents, immunomodulators, contraceptives, peptides, proteins, and sedatives.

Moreover, the latter can also fall into the class of diagnostic agents. In addition to the x-ray contrast media, such as, for example, iotrolan, iopromide, 3-carbamoyl-5-[N-hydroxyethyl)-acetamido]-2,4,6-triiodo-benzoic acid-[(1RS,2SR) -2,3-dihydroxy-1-hydroxymethylpropyl]-amide, 5-hydroxyacetamido -2,4,6-triiodophthalic acid-(2, 3-dihydroxy-N-methyl-propyl)-(2-hydroxy-methyl)-diamide, iodixanol, iohexol, iopamidol, iosimide or metrizamide, they also include NMR contrast media, such as, for example, the gadolinium complex of ethoxybenzyldiethylenetriaminepentaacetic acid, the Gd-DTPA, Gd-DOTA, Gd-BOPTA and Mn-DPDP (U.S. Pat. Nos. 4,957,399, 5,021,236 and Schuhmann-Giampieri, G., Inv. Radiol 28, 1993 in press).

The hydrophilic pharmaceutical substances that are used in the preparations according to the invention are generally distinguished by very quick renal elimination as well as good compatibility. In the case of the pharmaceutical agents used here, these can also be radiolabeled compounds.

The aqueous phase can, moreover, contain the adjuvants that are known to one skilled in the art, such as, for example, buffer substances, isotonizing additives, cryoprotectors or else water-soluble polymers, such as dextran or preservatives.

The lipid components that are used in the formulations according to the invention are generally described in the literature. Generally, for this purpose, these are phospholipids, such as, for example, phosphatidylcholine, phosphatidylethanolamine, phosphatidylglycerol, phosphatidylserine, phosphatidic acid, phosphatidylinositol or sphingolipids. Moreover, as additional components, sterols, such as, for example, cholesterol or else other components such as fatty acids (e.g., stearic acid, palmitic acid), dicetyl phosphate or cholesterol hemisuccinate, can be used. When using amphiphilic substances, such as, for example, hexadecylpoly(3)glycerol, dialkylpoly(7)glycerol ethers and alkyl glucosides, so-called niosomes, i.e., liposomes that consist of non-ionogenic vesicle formers, are obtained. Moreover, the liposome membrane can also contain preservatives, such as, for example, tocopherol as an antioxidant.

Further, the liposome membrane can also contain components, which modify the dispersion behavior of the liposomes in the blood. They include, e.g., PEGylated derivatives of phosphatidylethanolamine (e.g, DSPE-PEG), lipids, such as, for example, GM 1 or conjugates of sugars and hydrophobic components, such as, for example, palmitic or stearic acid esters of dextran. Moreover, corresponding liposomes can also be provided with components that specifically influence dispersion behavior in the body. For this purpose, these include so-called homing devices, such as, for example, antibodies. In addition, other components, such as, for example, enzymes or modified pharmaceutical substances (e.g., prodrugs), may also be components of the liposome preparation.

The liposome formulations according to the invention can be produced, for example, with the standard production processes that are described in the literature (e.g., Rubas, W. Schreler, H. or New, R. R. C.,—see above). With respect to the fact that inclusions of between 30 and 70% of the hydrophilic pharmaceutical substance are generally sought, preferably those methods in which large unilamellar liposomes (LUV) or multilamellar liposomes (MLV) are obtained are used. According to the invention, after the production of the liposome suspension, complete removal of the unencapsulated pharmaceutical substance is no longer necessary. In some cases where it is justified, however, partial concentration of the liposome suspension can be carried out by removing a portion of the unencapsulated pharmaceutical substance. In this case, the separating processes that are known to one skilled in the art are used. The liposome suspensions that are obtained in this respect can be stored directly or after adjuvants are added or first further processed (e.g., freeze-drying or spray-drying).

The liposome formulations with hydrophilic pharmaceutical substances according to the invention are stable with respect to determining the retention of the encapsulated components when stored in a refrigerator over a period of at least 3 months, but preferably more than 6 months. In especially suitable cases, corresponding shelf lives can also be achieved at elevated temperatures (for example, room temperature) with corresponding formulations. As an alternative, the liposome suspensions according to the invention can also be stored at lower temperatures (<0° C.).

Compared to the preparations known to date, the preparations according to the invention thus exhibit extremely good storage stability with simultaneously greatly reduced production expense (separation of the unencapsulated portion is omitted). The improved shelf life of the preparations according to the invention suggests that commercial use of such liposome formulations may be possible for the first time.

Surprisingly enough, it was noted that liposome formulations with an unencapsulated portion of pharmaceutical substance according to the invention also exhibit (in vitro) very high plasma-stability, which also mirrors formulations that correspond to in vivo data.

Further, it was noted that because the pharmaceutical substance in the formulations according to the invention is not separated, subsequent addition of isotonizing additives (e.g., NaCl) for adjusting osmotic pressure can often be omitted. This represents a further reduction of production expense, as well as minimizing the danger of negative influencing of the liposome quality (for example, vesicle size and inclusion) by corresponding foreign additives.

With respect to the medical use of directly stored formulations according to the invention, it is also advantageous that the latter can be prepared as ready-to-use suspensions as well.

Another aspect of the formulations according to the invention is the finding that the latter can be directly freeze-dried. In this case, macroscopically uniform lyophilizates with very good resuspension properties are obtained. The uniform structure of the lyophilizates as well as their resuspension behavior can in this case be attributed to the action of the unencapsulated pharmaceutical substance, which can perform the function of a skeleton former, for example. In special cases, moreover, the corresponding components can have a direct cryoprotective effect, which can result in partial or complete preservation of the liposome structure during freeze-drying depending on the concentration ratios.

The liposomes that are obtained after resuspension with the original amount of aqueous phase also have inclusions in the absence of standard cryoprotectors (e.g., sorbitol, trehalose), which correspond to those in the starting preparation. The lyophilizates thus produced are stable when stored in a refrigerator for a period of at least 3 months, but preferably for more than 6 months.

Another aspect of the preparations with an unencapsulated portion of pharmaceutical substance according to the invention is the fact that the presence of non-encapsulated material also offers some therapeutic or diagnostic advantages.

Thus, the free portion of pharmaceutical substance can be effective immediately after administration of corresponding preparations and in this connection can be used as, for example, an initial dose. This is primarily advantageous in so-called sustained-release systems in which therapeutically effective blood levels can be reached extremely quickly with such an initial dose, which then are maintained by the subsequently slow-release, encapsulated portion of pharmaceutical substance.

Also with respect to diagnostic uses, this free portion of pharmaceutical substance is very useful in order to be able to make statements about the condition of tissues, e.g., based on the different dispersion behaviors of the free and unencapsulated portions.

In the CT diagnosis of liver tumors, enhancement of the density of healthy liver tissue is carried out immediately after administration because of the unencapsulated portion, which is quickly eliminated. By the simultaneous successive concentration of the liposomal contrast medium (Kupfer cells), the density loss is then overcompensated, thus ensuring a longer-lasting high density enhancement.

In summary, it can be noted that because of their good retention of pharmaceutical substances in storage, the liposome formulations with an unencapsulated portion of pharmaceutical substance according to the invention offer the possibility for the first time of developing liposomal preparations with hydrophilic pharmaceutical substances for corresponding uses. The preparations according to the invention can, on the one hand, be stored immediately after production, without the unencapsulated portion having been completely separated in advance. As an alternative to this, these formulations can be further processed by, for example, freeze-drying. The processes or process steps that are used for the production of the liposome preparations according to the invention can all be considered standard methods that are also known in liposome technology.

Another special aspect of the preparations according to the invention is the fact that they often make it unnecessary to add additives. The same applies for cryoprotective additives, which in most cases are used in preparations that involve further freeze-drying.

The lyophilizates that are obtained after the liposome preparations according to the invention are freeze-dried are generally macroscopically uniform and can be easily resuspended. Moreover, the reconstituted liposome suspension exhibits inclusions that are greater than/equal to those in the starting suspensions.

In addition, liposome preparations according to the invention, which are obtained either by direct production or after reconstitution of, for example, freeze-dried or spray-dried products, in most cases exhibit high plasma stability in vitro and in vivo.

A special aspect of liposome suspensions according to the invention lies, moreover, in their special therapeutic/diagnostic properties as well as possible applications. This holds true especially for so-called sustained-release systems, in which the unencapsulated portion can be effective as an initial dose. In applications in imaging, additional diagnostically relevant findings can be made with the preparations according to the invention owing to the different dispersion behaviors of the free and encapsulated portions of active ingredient.

Embodiments:

The embodiments below are used for a more detailed explanation of the process according to the invention as well as the properties and applications of the products that are produced according to this process.

The abbreviations that are used in this respect are defined below:

| | |
|---|---|
| CH | Cholesterol, powdered cholesterol, Merck Company, Darmstadt |
| FEA | x-ray fluorescence spectroscopy |
| PCS | photon correlation spectroscopy, process for measuring particle sizes of under 1 $\mu$m (device: Nicomp 370) |
| SPC | soybean phosphatidylcholine, lipoid S 100, Lipoid KG Company, Ludwigshafen |
| SPG | soybean phosphatidylglycerol, lipoid SPG, lipoid KG Company |
| SS | stearic acid, Fluka, CH-Buchs |

EXAMPLE 1

Storage Stability of Liposome Formulations According to the Invention

Three liposome batches are produced with a standard extrusion method in combination with 3-freeze-thaw cycles after prior film formation. In this connection, SPC, CH and SPG are used as lipids at a molar ratio of 6:3:1 in a total concentration of 150 mg/g. As an aqueous phase, a solution of the nonionic, iodine-containing x-ray contrast medium iopromide in 20 mmol of tris-buffer (pH=7.5) is used, whereby the iodine concentration is 100 mg/g. After dispersion of the lipid film with the aqueous phase, the liposome dispersion is poured 5 times each sequentially over two polycarbonate membranes of increasing pore size (5.0/1.0/ 0.4/3×freeze-thaw/0.2 and 0.1 μm), whereby the three freeze-thaw cycles (freezing in methanol-dry ice and subsequent thawing in a water bath) are carried out after the passages through the 0.4 μm membranes.

The finished liposome suspensions are characterized immediately after production with respect to inclusion, pH and size, and they are then stored in a refrigerator without separating the unencapsulated pharmaceutical substance.

The respective properties of the three liposome batches at the beginning of storage as well as after 3 or 7 months of storage in a refrigerator are listed below as average values.

| Starting values: (n = 3) | Inclusion: | 40.2 ± 1.1% |
| --- | --- | --- |
| | Average diameter: | 104 ± 5 nm |
| | pH: | 7.2 ± 0.1 |
| Values at 3 months: | Inclusion: | 39.8 ± 1.2% |
| | Average diameter: | 109 ± 7 nm |
| | pH: | 7.2 ± 0.1 |
| Values at 7 months: | Inclusion: | 41.4 ± 0.4% |
| | Average diameter: | 123 ± 9 nm |
| | pH: | 7.2 ± 0.1 |

EXAMPLE 2

Freeze-Drying of Liposome Preparations According to the Invention

Iopromide-containing liposomes of lipid composition SPC/CH/SS 4:5:1 (molar) are produced by the ethanol evaporation method (Krause, W.; Sachse, A.; Wagner, S.; Kollenkirchen, U.; Rößling, G., Invest. Radiol. 26, S172–S174 (1991)) and then directly freeze-dried without separating the unencapsulated pharmaceutical substance in portions of about 20 ml in 50 ml infusion flasks (freezing –45° C., 5 hours and drying at about 50 Pa, 65 hours-GT 4, Leybold).

In this way, compact lyophilizate cakes are obtained that exhibit good resuspension properties. After resuspension with about 3 ml of 135 mmol mannitol solution per g of lyophilizate (dry weight), a liposome suspension with the properties listed below is obtained.

| Batch A1: (n = 3) | Total iodine content: | 91.9 ± 4.1 mg/g |
| --- | --- | --- |
| | Inclusion: | 36.5 ± 1.0% |
| | Average diameter: | 601 ± 13 nm |
| | Osmolality: | 507 ± 22 mOsm/kg |
| | pH: | 6.6 ± 0.1 |

After six months of storage in a refrigerator, the following values are determined according to identical resuspension:

| Total iodine content: | 93.3 ± 1.1 mg/g |
| --- | --- |
| Inclusion: | 39.6 ± 3.7% |
| Average diameter: | 581 ± 33 nm |
| Osmolality: | 493 ± 7 mOsm/kg |
| pH: | 6.6 ± 0.1 |

EXAMPLE 3

Plasma Stability of Liposome Formulations According to the Invention

Liposome lyophilizates are produced as described in Example 2 and resuspended. Then, portions of the liposome suspension thus obtained were mixed with rabbit plasma, whereby an iodine concentration of about 5 mg/ml is set. In each case, 1 ml of this plasma is then dialyzed in a Dianorm equilibrium dialysis apparatus (Dianorm, Heidelberg) from 20 mmol of tris-buffer (pH=7.5) by dialysis membranes with a cutoff of 5000 Da (Dianorm). At different times, samples of the retentate (plasma) and permeate side (buffer) are taken, and the iodine content is determined using x-ray fluorescence spectroscopy (FEA-Kauman, L.; Deconninck, F. et al., Invest. Radiol 11, 210–215 (1976)). The leakage of the pharmaceutical substance at different times can be calculated from this.

During the first 4 hours, a leakage of about 5% in rabbit plasma is noted. After 24 hours, the leakage is only 9%, which confirms the extreme plasma stability of these liposomes.

EXAMPLE 4

Organ Dispersion (Rats) of Liposome Formulations According to the Invention

A liposome formulation is produced according to Example 1, whereby unlike this example, the lipid concentration used is only 100 mg/g. Moreover, it is extruded only 5 times over 5.0 and 1.0 μm polycarbonate membranes here, and then three freeze-thaw cycles are carried out. Then, repeated extrusion via 0.4 μm membranes (10 passages) follows. The liposomes thus obtained exhibit a total iodine content of 81.6 mg/ml, an inclusion of 32.0%, an osmolality of 263 mOsm/kg, and an average diameter of 162 nm.

The liposomes are injected at a dose of 250 mg of total iodine/kg in 5 male rats (weight (390–425 g) each, and the animals are sacrificed 1 hour after injection. Then, livers, spleens, lungs, kidneys and blood are removed, and their iodine contents are determined by means of FEA.

The content of blood, determined at this time at about 27% of the total dose, which reflects the high plasma stability of this preparation, is noteworthy.

At this time, a major part of the unencapsulated portion is already excreted.

EXAMPLE 5

Liver Concentration (in Rats) of Liposome Formulations According to the Invention A resuspended liposome suspension that is produced according to Example 2 is injected at doses of 100, 300 and 1000 mg of total iodine/kg of body weight in female rats (weight: about 200 g), and the density enhancement in the liver (ΔHU) is ascertained over a period of 90 minutes with the aid of a computer tomograph (Somatome Plus, Siemens; 120 kv, 250 mA, 2*1 s, 2 mm layer thickness). The values that are obtained are listed in the table below.

TABLE 1

Relative Density Enhancement (HU) in the Rat Liver After Administration of Liposomes

| Time [minutes] | 100 mg of I/kg of body weight | 300 mg of I/kg of body weight | 1000 mg of I/kg of body weight |
| --- | --- | --- | --- |
| 1 | 14.8 | 28.7 | 76.3 |
| 7.5 | 16.9 | 36.2 | 83.9 |
| 15 | 12.6 | 34.4 | 88.6 |

TABLE 1-continued

Relative Density Enhancement (HU) in the Rat Liver
After Administration of Liposomes

| Time [minutes] | 100 mg of I/kg of body weight | 300 mg of I/kg of body weight | 1000 mg of I/kg of body weight |
|---|---|---|---|
| 30 | 17.4 | 31.4 | 64.5 |
| 60 | 12.1 | 25.5 | 52.6 |
| 90 | 9.0 | 21.5 | 57.5 |

As the table shows, density enhancement in the liver occurs even at very early times, which can first be attributed primarily to the free portion of the contrast medium. At later times (>15 minutes), the density enhancement is then outweighed by the liposomally encapsulated portion as a result of the liposomes being taken up in the Kupfer cells.

What is claimed is:

1. A method for diagnostic imaging of the liver of the patient, which comprises imaging for diagnostic purposes the liver of a patient who has been administered a liposome suspension containing a hydrophilic contrast medium wherein 30 to 70% by weight of the contrast medium is encapsulated in liposomes and the remaining contrast medium is not encapsulated in liposomes, such that the combined action of the unencapsulated contrast medium and the encapsulated contrast medium results in a long-lasting high density enhancement of the healthy liver tissue.

2. The method of claim 1, wherein the high density enhancement of the healthy liver tissue is achieved for at least from 1 minute after administration to from 60 minutes after administration.

3. The method of claim 1, wherein the contrast medium comprises a triodobenzoic acid x-ray contrast media.

4. The method of claim 1, wherein the contrast medium comprises iopromide.

5. The method of claim 1, wherein the contrast medium comprises 3-carbamoyl -5-[N-(2-hydroxy-ethyl)-acetamido]-2,4,6-triiodobenzoic acid-[(1RS,2RS)-2,3-dihydroxy-1-hydroxymethylpropyl]-amide.

6. The method of claim 1, wherein the contrast medium comprises 5-hydroxyacetamido-2,4,6-triiodo-isophthalic acid-(2,3-dihydroxy-N-methyl-propyl)-(2-hydroxyethyl)-diamide.

7. The method of claim 1, wherein the contrast medium comprises iotrolan.

8. The method of claim 1, wherein the contrast medium comprises a NMR contrast agent.

9. The method of claim 8, wherein the NMR contrast medium comprises the gadolinium complex of ethoxybenzyldiethlyenetriaminepentaacetic acid.

10. The method of claim 8, wherein the liposomes in the liposome suspension comprise phospholipids.

* * * * *